(12) United States Patent
Kienzle, III

(10) Patent No.: US 6,718,194 B2
(45) Date of Patent: Apr. 6, 2004

(54) COMPUTER ASSISTED INTRAMEDULLARY ROD SURGERY SYSTEM WITH ENHANCED FEATURES

(75) Inventor: Thomas C. Kienzle, III, Lake Forest, IL (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 275 days.

(21) Appl. No.: 09/683,107

(22) Filed: Nov. 19, 2001

(65) Prior Publication Data

US 2002/0077541 A1 Jun. 20, 2002

Related U.S. Application Data

(60) Provisional application No. 60/249,697, filed on Nov. 17, 2000.

(51) Int. Cl.$^7$ .................................................. A61B 5/05
(52) U.S. Cl. ..................... 600/424; 600/427; 606/130; 378/20
(58) Field of Search ........................ 600/300, 407–473; 606/62, 64, 72, 73, 86, 87, 98, 102, 105, 130; 378/4, 20, 205; 128/898, 916, 922, 923

(56) References Cited

U.S. PATENT DOCUMENTS

| | | | |
|---|---|---|---|
| 4,976,713 A | | 12/1990 | Landanger et al. |
| 5,031,203 A | | 7/1991 | Trecha |
| 5,274,551 A | | 12/1993 | Corby, Jr. |
| 5,411,503 A | | 5/1995 | Hollstien et al. |
| 5,478,343 A | | 12/1995 | Ritter |
| 5,540,691 A | | 7/1996 | Elstrom et al. |
| 5,748,767 A | | 5/1998 | Raab |
| 5,769,092 A | * | 6/1998 | Williamson, Jr. ............ 128/898 |
| 5,920,395 A | | 7/1999 | Schulz |
| 5,987,349 A | | 11/1999 | Schulz |
| 6,074,394 A | | 6/2000 | Krause |
| 6,081,741 A | | 6/2000 | Hollis |
| 6,167,296 A | * | 12/2000 | Shahidi ....................... 600/427 |
| 6,285,902 B1 | | 9/2001 | Kienzle, III et al. |

OTHER PUBLICATIONS

Viant, et al. "A Computer Assisted Orthopaedic System for Distal Locking of Intramedullary Nails" Medimec '95, Bristol, UK.

Hofstetter, et al. "Fluoroscopy Based Surgical Navigation—Concept and Clinical Applications" Proceedings of the 11th International Symposium and Exhibition, Computer Assisted Radiology and Surgery, Berlin.

Yaniv, et al. "Fluoroscopic Image Processing for Computer–Aided Orthopaedic Surgery" Proceedings of the 1st International Conference on Medical Image Computing and Computer–Assisted Intervention, Cambridge, MA.

Hofstetter, et al. "Fluoroscopy as an Imaging Means for Computer Assisted Surgical Navigation" Computer Aided Surgery, 4:65–76.

Suhm, et al. "Surgical Navigation Based on Fluoroscopy—Clinical Application for Computer–Assisted Distal Locking of Intramedullary Implants" Computer Aided Surgery, 5:391–400.

\* cited by examiner

Primary Examiner—Ali M. Imam
(74) Attorney, Agent, or Firm—McAndrew, Held & Malloy, Ltd.; Peter J. Vogel; Michael A. Dellapenna

(57) ABSTRACT

A computer assisted surgery system is described for assisting a surgeon in aligning a drill with the interlocking holes of an implanted intramedullary (IM) rod used for fixation of long bone fractures. With the IM rod inserted, a localizing device measures the pose of a tracked adapter attached to the rod's exposed end. Approximate AP and lateral fluoroscopic x-ray images are acquired of the end of the rod with the interlocking holes. Image processing algorithms determine the actual position of the rod and calculate an adjustment to the pose of the tracked adapter and IM rod. Using the adjusted pose information, the system displays, in three roughly orthogonal views, a representation of the drill trajectory relative to the images of the IM rod and relative to a graphic representation of the IM rod.

13 Claims, 5 Drawing Sheets

COMPUTER ASSISTED INTRAMEDULLARY ROD SURGERY SYSTEM WITH ENHANCED FEATURES

BACKGROUND OF INVENTION

This invention relates to a computer assisted surgery system for use in inserting interlocking screws in an intramedullary rod.

A current surgical treatment for fractures of the shaft of long bones (e.g., femur and tibia) is the insertion of an intramedullary rod (IM rod). These devices are relatively rigid devices inserted into one end of the bone and down the center canal of the bone shaft, such that the fracture site is bridged. Transverse holes in either end of the IM rod receive screws inserted transversely through the bone in order to lock the two bone fragments relative to one another. The insertion of the screws farthest from the IM rod insertion hole is currently a difficult and time consuming procedure requiring numerous x-ray images. An intraoperative x-ray machine (C-arm) is repeatedly fired and reoriented until it is exactly aligned with the transverse holes as evidenced by x-ray images displaying the holes as "perfect circles". To establish a starting point, the surgeon uses further x-ray images to align the drill tip with the images of the holes. The surgeon then uses the source-to-receiver axis of the C-arm as an external reference frame along which the long axis of the drill is oriented. Even after this, several attempts may be required to drill the holes into the bone and through the transverse holes.

Several alternative approaches have been employed in an attempt to speed this process. External jigs have been tried with little success because inaccuracies in the jig, inaccuracy of the mounting between jig and IM rod, and deformation of the IM rod accumulate to cause the final jig hole positions to be unreliably aligned with the IM rod holes. Radiolucent drills and drill guides and laser sighting devices have been developed which, in the best cases, improve the speed and accuracy of hole placement, but still require a significant number of x-ray images to be obtained in order to first achieve a C-arm orientation that produces "perfect circles" in the images.

Image-guided approaches have been developed, but these too require the "perfect circle" alignment of the C-arm. Most image guided systems display the drill trajectory over "perfect circle" images of the IM rod. One system assists the surgeon in correctly orienting the C-arm to obtain "perfect circles": "Surgical Navigation Based on Fluoroscopy Clinical Application for Computer-Assisted Distal Locking of Intramedullary Implants", Suhm, et.al., Computer Aided Surgery 5:391–400, 2000. Another difficulty with existing image guided systems is that the surgeon must align the drill guide while viewing an "end on" representation of the drill guide, which can be quite challenging.

Several devices have been described (U.S. Pat. Nos. 5,411,503, 5,540,691, 6,074,394, 6,081,741) in which an emitter is inserted into the IM rod, down to the level of the interlocking holes, and transducers on the drill guide report the position of the drill trajectory relative to the holes. These devices, however, require equipment dedicated to this one surgical task, require the extra step of inserting an emitter to the level of the hole, and typically provide only rudimentary "end on" representations of the drill trajectory.

U.S. Pat. No. 6,285,902, incorporated herein by reference, entitled "Computer Assisted Targeting Device for Use in Orthopaedic Surgery" describes a system in which, preferably, orthopaedic surgical tools outfitted with infrared LEDs are tracked by an optical localizing device. The poses of these tools are determined and graphic representations of the tools are superimposed on standard intraoperative x-ray images. This allows the surgeon to view, in real time, the position of the tool or tools with respect to an imaged body part or another tool or tools. In the preferred embodiment, a drill guide outfitted with infrared LEDs is tracked and the trajectory of its bore is displayed on the x-ray image of the involved bone. This allows a surgeon to accurately predict the trajectory of a guide pin that passes through the bore of the drill guide. The guide pin, once inserted, is used as a reference for the insertion of implantable cannulated screws.

An alternative embodiment of the previous invention, described in the referenced patent, allows its use in the insertion of distal interlocking screws in an intramedullary (IM) rod by displaying the drill guide trajectory relative to a computer generated representation of a cross-section of the IM rod. The current invention is an enhancement to the previous invention that adjusts the graphic representations of the IM rod based on information developed from the x-ray images. This facilitates the more accurate alignment of a drill through the holes and eliminates the need to align the x-ray beam with the holes in the IM rod. This can significantly reduce the amount of radiation involved in the procedure and reduce the time required to insert the screws.

SUMMARY OF INVENTION

Accordingly, one objective of the present invention is to provide a computer assisted surgery system for positioning an instrument relative to a portion of a surgical implant. More specifically, it assists a surgeon in drilling a hole through a long bone and through transversely oriented holes in an intramedullary rod (IM rod) during a fracture fixation procedure regardless of deformation of the IM rod.

Another objective of the invention is to provide a technique and apparatus for accurately displaying the trajectory of the drill relative to the holes of the IM rod.

Still another objective of the invention is to provide a technique and apparatus for using x-ray images of the IM rod to accurately determine the locations of the holes.

These and other objects of the present invention are achieved by the use of a computer assisted surgery system, including a computer, a localizing device and a display monitor. The system also includes a tracked adapter attached to the IM rod and a drill guide, both of which have their poses determined by the localizer. With the IM rod inserted in a long bone, and the tracked adapter attached to the exposed end of the IM rod the pose of the adapter and the IM rod are measured by the localizing device. Two approximately orthogonal x-ray images are then obtained of the IM rod in the vicinity of the holes. Image processing techniques are used to accurately determine the location of the IM rod from the x-ray images and an adjusted pose is calculated for the IM rod. A graphic representation of the drill trajectory is displayed superimposed over the images of the IM rod and over a graphic representation of the IM rod, in order to assist the surgeon in placing the drill in the proper position relative to the IM rod holes.

DETAILED DESCRIPTION

Figure 1:
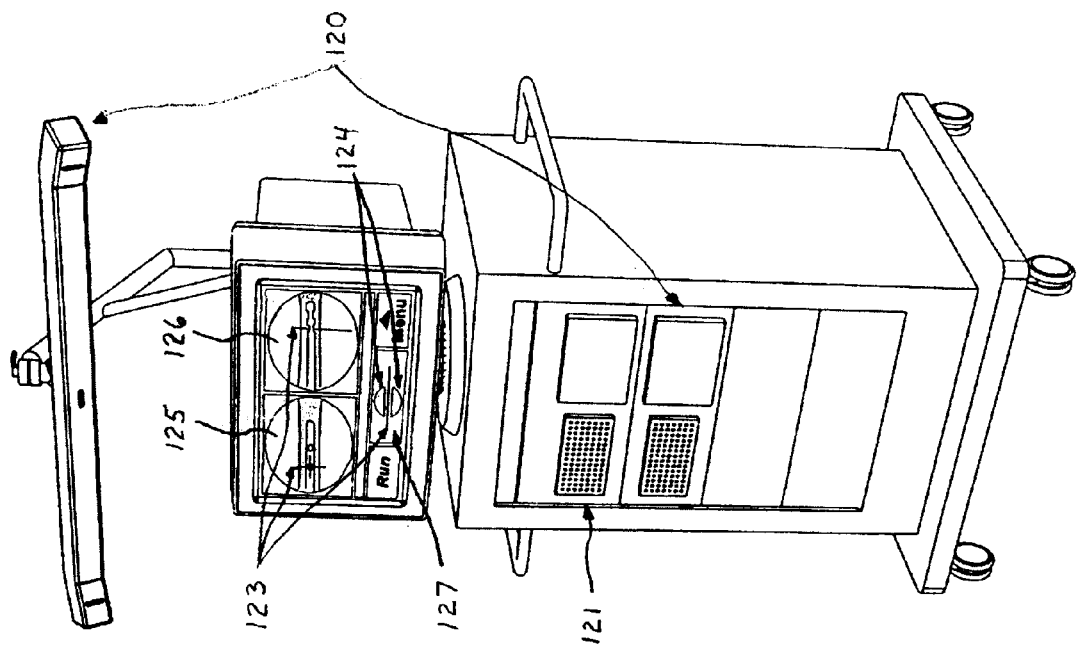
FIG. 1 is a perspective view of an intramedullary rod inserted into a femur, a tracked adapter attached to the intramedullary rod, a drill guide, a partial C-arm, the computer assisted surgery system with localizer camera and display screen containing images and graphics.
Figure 1:
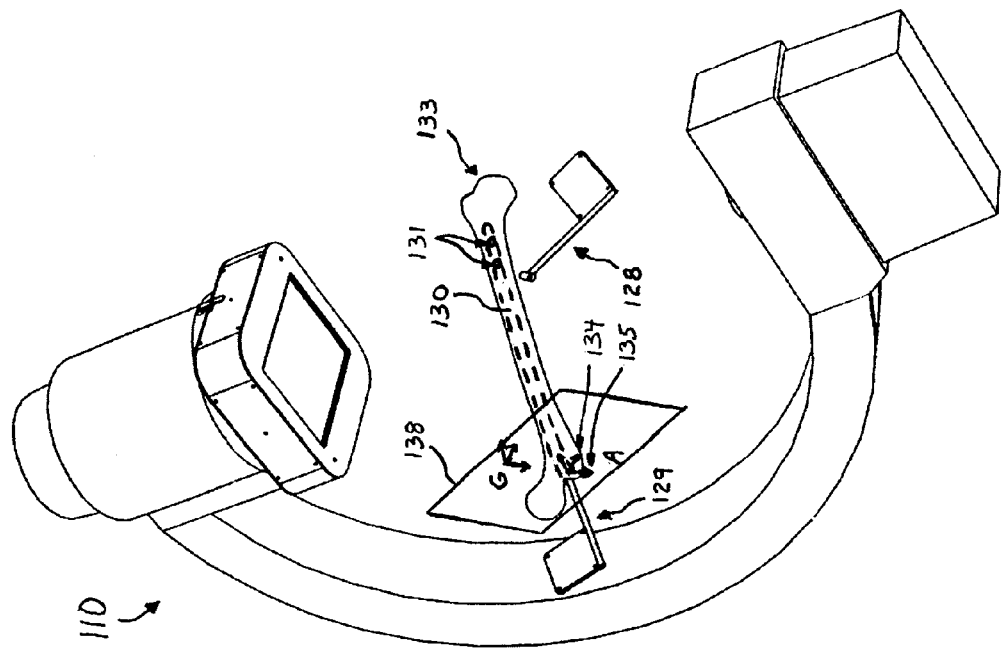

An embodiment of the image guided system of U.S. Pat. No. 6,285,902 teaches a system for placing distal interlocking screws in an IM rod. As shown in FIG. 1, the system is based on a computer (121) that receives input from an x-ray imaging device (110) and a localizing device (120), and displays surgical instrument representations (123) over x-ray images (125 and 126) in real time. A tracked adapter (129) is attached to the exposed end of the inserted IM rod (130) such that the pose of the rod can be tracked. A drill guide (128) is also tracked, and a representation of its trajectory (123) is overlaid on x-ray images (125 and 126) of the IM rod (130). Additionally, the system displays, in a separate window (127), the drill guide trajectory (123) relative to a graphical representation (124) of a cross-section of the IM rod (130) at the level of the transverse interlocking holes (131) by projecting models of these instruments onto a picture plane (138). During the procedure, the surgeon uses the AP image (126) of the IM rod (130) to align the drill guide (128) in the coronal plane, and the lateral image (125) and the cross sectional graphic (124) to align the drill guide (128) in the axial plane.

Figure 2:
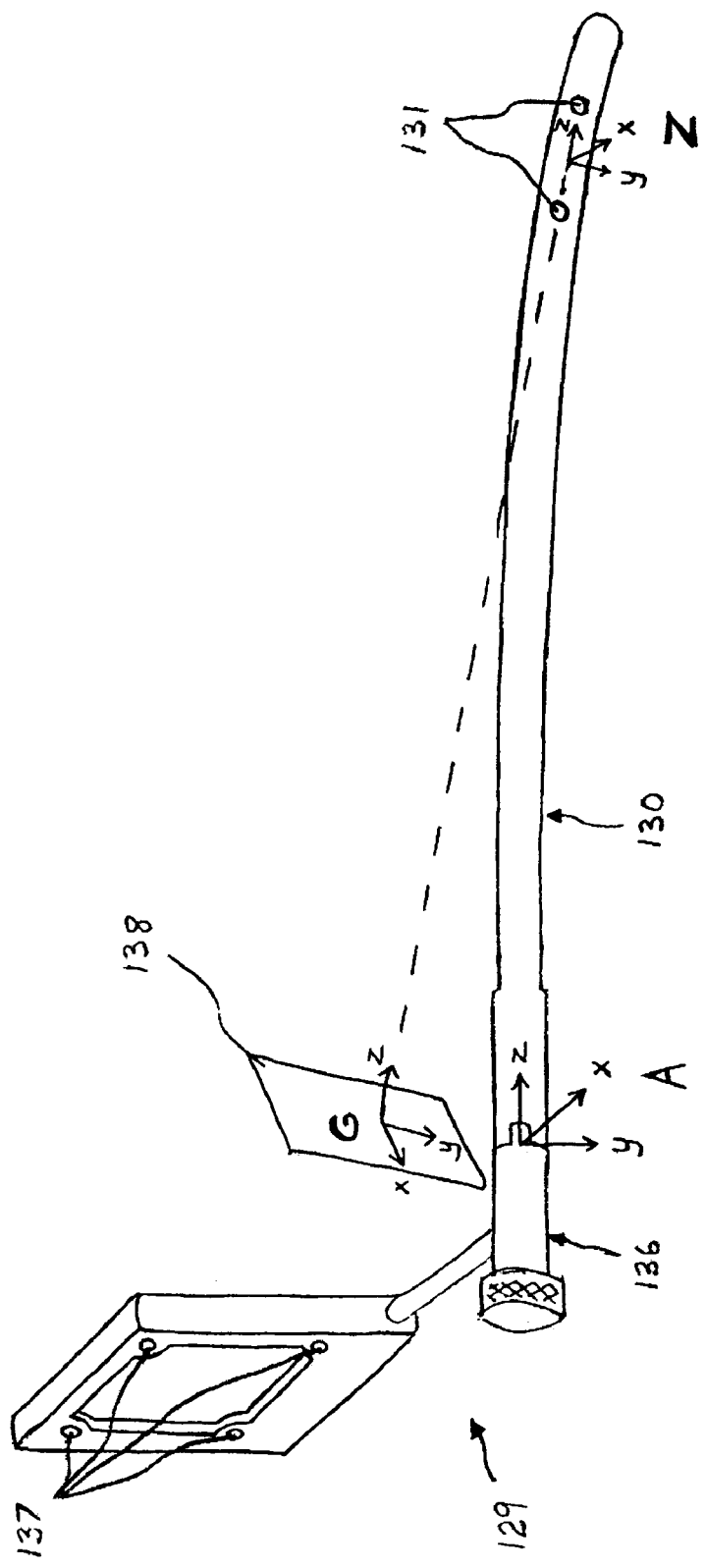
FIG. 2 is a perspective view of the intramedullary rod with attached tracked adapter.

The current invention improves upon the previous invention by providing greater accuracy in generating the graphic representations (124) of the IM rod (130) relative to the drill guide (128), regardless of bending of the IM rod (130) or minor errors in attaching the adapter (129) to the IM rod (130). This improvement allows the surgeon to use these relative graphic representations (124 and 123) alone to exactly align the drill guide (128) in the axial plane. While the surgeon still uses the AP view (126) to align the drill guide (128) in the coronal plane, there is no longer a need to rely on the lateral view (125), thus avoiding the difficulty of positioning a drill guide (128) using an "end-on" representation, during the axial alignment of the trajectory. It also eliminates the need for the surgeon to estimate the required anteroposterior position of the drill guide tip based on the distance between the IM rod and the femoral shaft cortex and the amount of axial rotation of the IM rod. In the preferred embodiment, the IM rod (130) is inserted in the long bone (133) in the usual manner. While the invention will be preferably described for drilling holes in the bone (133) for the interlocking holes (131) in the end of the IM rod farthest from the exposed end, the system may be alternately used for all interlocking screws and associated implants. As shown in FIG. 2, a tracking device (129), preferably comprising an adapter (136) to the IM rod (130) and an array of three or more localizing emitters (137), is attached to the exposed end of the IM rod (130). The exposed end of the IM rod (130) is keyed to the adapter (136) such that the adapter (136) is attached to the inserted rod in a unique manner and the relationship is known within the limits of error of attachment preferably to within a few degrees and a few millimeters. A coordinate frame, A, is defined preferably at the interface between the IM rod (130) and the tracking device (129) and is in a known and fixed relationship to the localizing emitters (137). Computer models of the features of the tracking adapter (129) and IM rod relative to coordinate frame A and graphic representations of features of the IM rod (130) relative to coordinate frame A are stored in the computer's long term memory. A second coordinate frame, Z, is defined relative to the localizing emitters (137) of the tracking device (129) and is preferably located on the IM rod (130) halfway between the transverse holes (131). It is oriented with the z-axis coincident to the long axis of the IM rod (130) and the x-axis parallel to the bore of the transverse holes (131). Another coordinate frame, G, is selected relative the localizing emitters (137) such that its x-axis and y-axis define a picture plane (138) upon which instrument representations may be projected to form an image for display. The z-axis of coordinate frame G is preferably oriented such that it passes through the centers of both distal transverse holes (131), thus causing representations of both distal transverse holes (131) to project to the same location on the picture plane (138). Alternatively, the picture plane (138) may be selected in any pose that is near-orthogonal (e.g., within 20 degrees) to the long axis of the IM rod without departing from the instant invention. Further, separate picture planes may be selected for each transverse hole through which the system is to assist the surgeon in inserting a screw.

Figure 3:
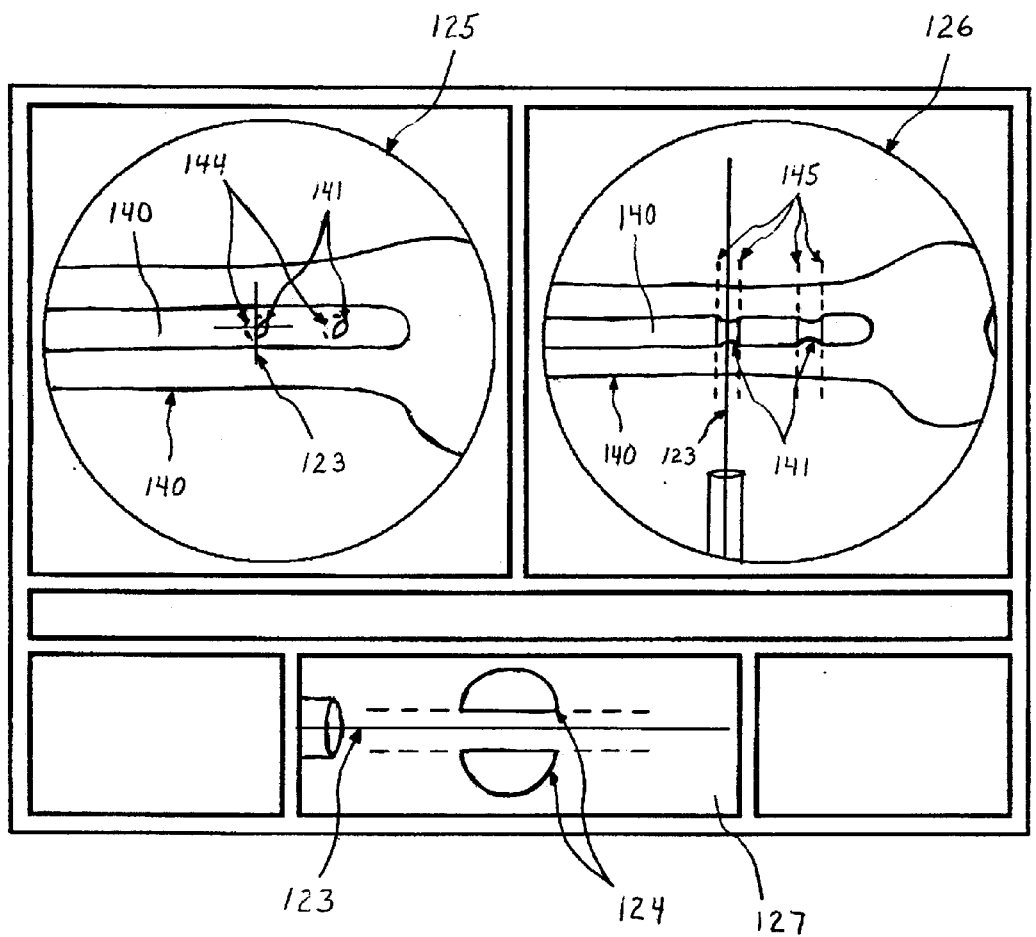
FIG. 3 is an example of a screen display of two images and a generated graphic with superimposed instrument representations.

With the tracking device (129) attached to the IM rod (130) and its pose being read by the localizing device, a graphic representation of the IM rod (130) is projected onto the picture plane (138) defined by coordinate frame G. Because the picture plane (138) is defined to be substantially perpendicular to the long axis of the IM rod (130), the image projected on it will be an "end-view" of the IM rod graphic representation. This end-view image is projected onto the picture plane (138) and, as shown in FIG. 3, is transformed into a graphic representation (124) of the IM rod and displayed in a field (127) of the display screen. The software can display different versions of an instrument representation for different viewing angles. The end-view version of the IM rod representation (124) is a pair of semicircles representing the cross section of the IM rod (130) with a gap between them representing the transverse holes (131). Virtual lines are additionally displayed as dashed lines extending from the straight portion of the semicircles to emphasize the orientation of the transverse screw holes (131). The purpose of this representation (124) is to provide the surgeon with improved information regarding the orientation and location of the transverse holes (131) in the axial plane.

Returning to FIG. 1, the C-arm (110) acquires x-ray images (125 and 126) of the bone (133) that include the transverse holes (131) of the inserted IM rod (130). These images (125 and 126) need not be exactly anteroposterior or exactly lateral with respect to the IM rod (130) (i.e., "perfect circles" need not be obtained). The C-arm (110) need be oriented only to within about 30 degrees of exactly AP or lateral, and the misalignment may be either axial or oblique. The pose of the C-arm (110) and the pose of the tracking device (129) and its related coordinate frame A are calculated by the localizing device (120) when the image is acquired. If the x-axis (134) or y-axis (135) of coordinate frame A is within, preferably, 30 degrees of the source-receiver axis of the C-arm (110), then the image is considered lateral or anteroposterior (AP) respectively.

If the acquired image is determined to be an AP view then, as shown in FIG. 3, the software will generate an AP version of the graphic representation (145) of the IM rod which is intended to highlight the transverse holes (131). This graphic representation (145) is defined relative to coordinate frame A, and is overlaid onto the AP image (126) of the IM rod (130). This AP version of the IM rod representation (145) comprises lines along the sides of the transverse holes' image (141), with dashed virtual lines extending from either side to emphasize the orientation of the holes (141). The drill guide representation (123) is displayed relative to the IM rod representation (145) as both are overlaid on the AP image (126) and improves the surgeon's ability to accurately align the drill guide (128) with the IM rod transverse holes (131) in the coronal plane.

If the acquired image is determined to be a lateral view then the software will optionally generate a lateral version of the graphic representation (144) of the transverse holes (131). This graphic representation (144) comprises two circles representing the openings of the two holes. It is overlaid on the transverse holes (141) seen in the lateral image (125) to improve the surgeons ability to identify the starting point for the drill. However, this is of less importance when compared to the utility of the cross-sectional graphic (127).

Alternatively, the graphic representation (124, 144 and 145) of the IM rod (131) may take other forms including 3-D surface models, bitmaps, or other wireframe models. Any version of the graphic representations (124, 144 and 145), regardless of view orientation, that provides the surgeon with sufficient information to orient the drill guide (128) relative to the IM rod (130) in a given plane may be used without departing from the instant invention.

Figure 4:
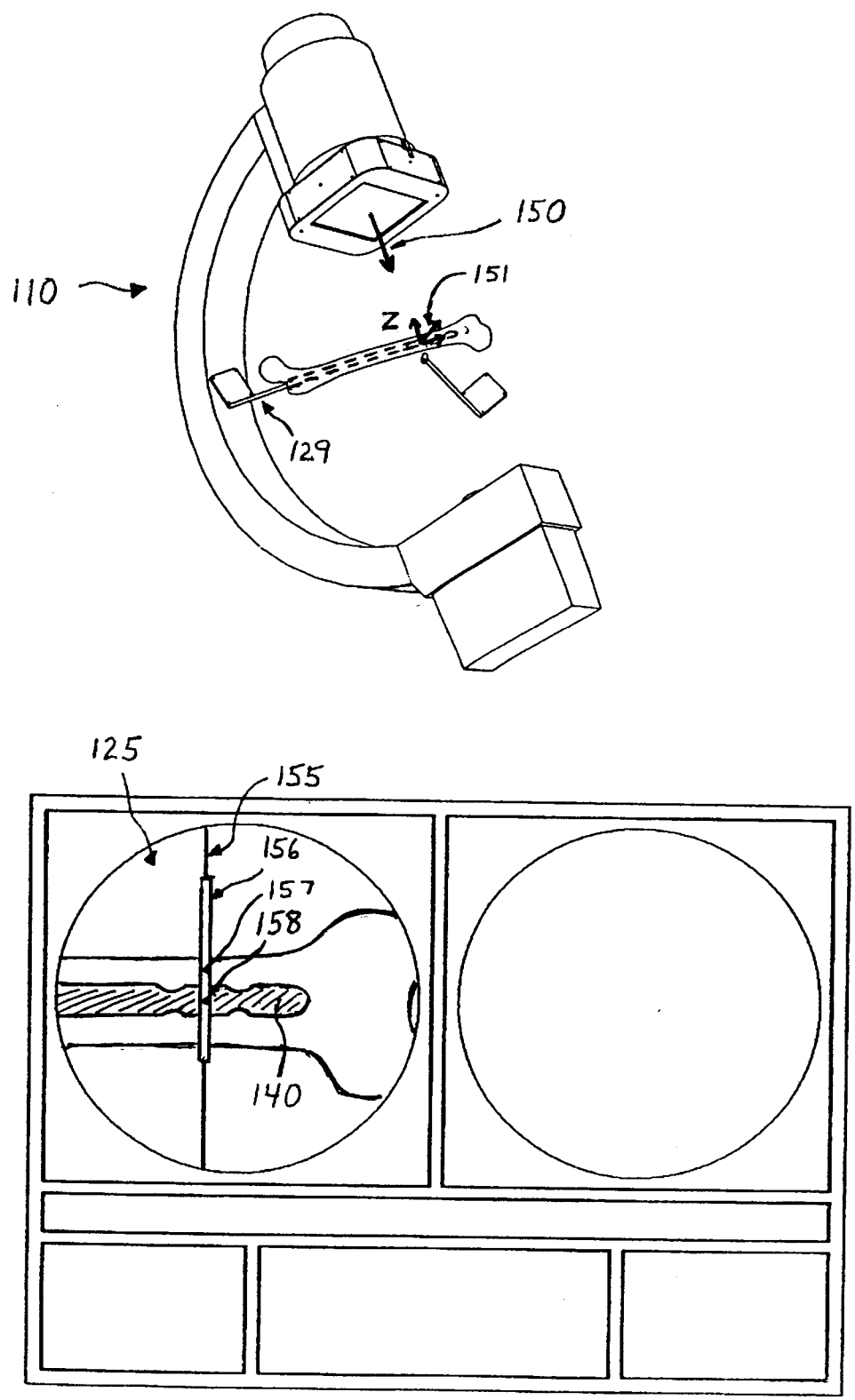
FIG. 4 is a perspective view of an intramedullary rod inserted into a femur, a tracked adapter attached to the intramedullary rod, a drill guide, a partial C-arm, and a example of a screen display of an image with superimposed graphics.

Additionally, as each image is acquired, adjustment of the position of the graphic representation (124, 144, and 145) of the IM rod (130) is performed to correct for any deviation due to flexure of the IM rod (131) or inaccuracies in attachment of the tracking device (129) or other conditions leading to inaccuracies in localizing the IM rod (130). Turning to FIG. 4, the poses of the IM rod tracking device (129) and the C-arm (110) are recorded at the time of image acquisition. If the C-arm source-receiver axis (150) is within, preferably, 30 degrees of the x-axis or y-axis of coordinate frame Z then adjustment is to be performed along the y-axis or x-axis, respectively. While the following adjustment steps are illustrated in FIG. 4, they are preferably performed without being displayed to the user. The adjustment is accomplished by projecting this adjustment axis (151) of the Z coordinate frame, onto the acquired image (125) using the conic projection model, and then analyzing the image data along a specific segment (156) of this projected line (155). Image processing techniques known to those skilled in the art threshold the image data within the image data segment (156) and find the center (158) of the radio-opaque IM rod image (140). The difference between this image location (158) and the projected origin (157) of coordinate frame Z is calculated and the difference value stored. Alternatively, any image processing techniques, or other means for directly measuring the positional error of the IM rod (130) at or near the transverse holes (131) may be used without departing from the instant invention.

When the difference value for AP, lateral, or both images have been processed, the corresponding Z frame x-axis and y-axis components are calculated by techniques known in the art. These difference components are then used to develop an adjustment transformation. Returning to FIG. 3, this adjustment transformation is applied to coordinate frame A, causing it to rotate such that the IM rod's AP and lateral graphic representations (144 and 145) defined relative to A, will align with the IM rod's x-ray images (140). After the adjustment rotations, the positions of the cross sectional representation (124), the AP representation (145), and the optional lateral representation (144), which are displayed to the user, more accurately represent the actual position of the IM rod (130).

Alternately, the overlay of the graphic representations (124, 144 and 145) may be corrected by the translation of coordinate frame A instead of by rotation. Or, instead, the graphic representations (124, 144 and 145) could be altered to effect the correction. For example, if the total difference is attributed to bending of the rod, the coordinate frame A could be left unchanged and the graphic representations (123, 144 and 145) could be altered to simulate the flexure of the IM rod (130). Any correction means that uses the difference between the expected and actual positions of the IM rod (130) to modify its graphic representation in such a way to make it more accurate may be used without departing from the instant invention.

Figure 5:
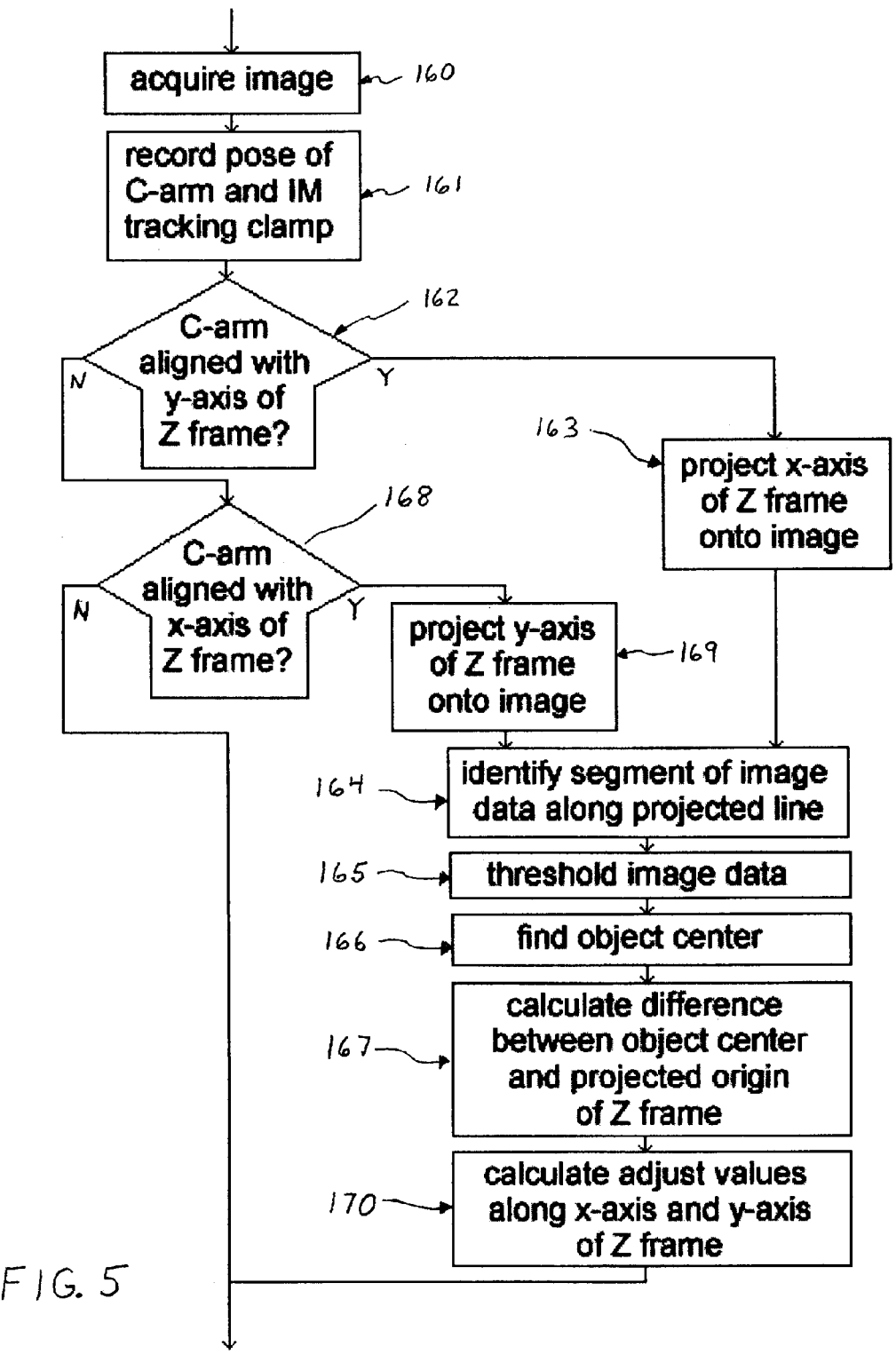
FIG. 5 is a diagrammatic illustration of the software operation during pose adjustment.

In summary, the software steps required are shown in FIG. 5. The image is acquired (160) and the poses of the C-arm and tracking clamp determined (161). If the y-axis of the Z coordinate frame is near-aligned with the C-arm (162) then project the Z frame x-axis onto the image (163), isolate an appropriate segment of image data along the projected line (164), apply a thresholding algorithm to emphasize the IM rod (165), find the center of the IM rod in the image data (166), and calculate the difference between the center of the IM rod's image and the projected Z-frame's origin as modeled (167). If the x-axis of the Z frame is near aligned with the C-arm (168) then project the y-axis onto the image (169) and perform the image processing steps above (164–167). Calculate an adjustment transformation based on available x-axis and y-axis difference values (170).

Returning to FIG. 1, once the corrected IM rod representations (124 and 144 and 145 seen best in FIG. 3) are being displayed, the surgeon prepares to drill the holes in the bone (131). The drill guide (128) generates a trajectory (123) that overlays both image fields (125 and 126) and projects onto the graphics field (127) as well. As shown in FIG. 3, the surgeon aligns the drill trajectory (123) to pass through the hole markers of the AP IM rod representation (145) and through the hole path on the cross sectional IM rod representation (124) in the graphics field (127). Once the proper alignment is achieved, the drill is advanced in the drill guide (128). The second hole is prepared in a similar fashion and confirmatory x-rays are obtained prior to inserting appropriately sized screws. Alternately, self-tapping screws may be directly inserted with a suitable instrument.

While the above description relates to the placement of interlocking screws in intramedullary rods placed in long bones, persons skilled in the art will recognize the applicability of this invention to other devices in other locations of the body such as the insertion of screws into other implantable devices. Any procedure wherein a first device is positioned relative to a second device at a position that is not known with sufficient accuracy by use of a localizing device can be performed in a more accurate manner with this invention.

What is claimed is:

1. A computer assisted surgery system for positioning a surgical instrument relative to a surgical implant within a patient's body, said system comprising:
   a surgical instrument defining a trajectory;
   a surgical implant with one or more holes;
   a localizing device for measuring the pose of the surgical instrument and the pose of the surgical implant;

means for acquiring x-ray images of the surgical implant;

means for calculating an adjusted pose for the surgical implant, said means for calculating the adjusted pose based on information developed from the x-ray images; and means for displaying a graphic representation of the trajectory relative to a graphic representation of the surgical implant, based on the measured pose of the surgical instrument and the adjusted pose of the surgical implant;

wherein the adjusted pose of the implant compensates for deformation of the implant or inaccuracies in localization, so as to assist a surgeon in aligning the trajectory of the surgical instrument with the holes in the surgical implant.

2. The computer assisted surgery system of claim 1 wherein the information developed from the x-ray images is an adjustment to be applied to the pose of the implant, said adjustment developed through image processing techniques applied to the x-ray images of the implant.

3. A method for positioning a surgical instrument relative to a surgical implant, the method comprising:
(a) generating a computer model of the surgical implant;
(b) generating a computer model of a tracked adapter;
(c) attaching the tracked adapter to the surgical implant;
(d) measuring the pose of the tracked adapter with a localizing device;
(e) calculating the pose of the implant from the measured pose of the tracked adapter, the computer model of the tracked adapter, and the computer model of the implant;
(f) calculating a first position in space of a reference point on the implant based on the model of the implant and the calculated pose of the implant;
(g) acquiring two approximately orthogonal 2-D images of the implant;
(h) calculating a second position in space of the reference point on the implant based on its position in the images;
(i) adjusting the calculated pose of the implant based on the difference between the first and second calculated positions of the reference point on the implant;
(j) measuring the pose of the surgical instrument with the localizing device; and
(k) displaying a graphic representation of the surgical instrument relative to a graphic representation of the implant based on the measured pose of the surgical instrument and the adjusted pose of the implant.

4. The method of claim 3 wherein adjusting the calculated pose of the implant comprises adjusting the graphic representation of the implant.

5. The method of claim 3 wherein calculating a second position of the reference point comprises the processing of the images to extract the locations of edges of the implant.

6. The method of claim 3 wherein displaying a graphic representation of the surgical instrument relative to the graphic representation of the implant includes the projection of representations on a picture plane approximately orthogonal to the two 2-D images.

7. The method of claim 3 further comprising the step of displaying the graphic representation of the surgical instrument superimposed on the 2-D images.

8. A method for accurately drilling holes into a long bone so that the holes are aligned with the interlocking holes of an intramedullary rod, the method comprising the steps of:
(a) inserting the intramedullary rod into the bone so as to leave one end of the rod exposed, the opposite end having one or more transverse holes disposed therein, the rod defining a long axis;
(b) attaching a tracked adapter to the exposed end of the rod, the pose of said tracked adapter measurable by a localizing device;
(c) defining a coordinate frame G relative to the tracked adapter such that its x-axis and y-axis define a picture plane upon which graphic representations of the intramedullary rod and surgical instruments may be projected for display to a surgeon;
(d) projecting the graphic representation of the intramedullary rod onto the picture plane defined by coordinate frame G such that an end view of the graphic representation of the intramedullary rod is displayed;
(e) acquiring one or more x-ray images of the long bone including the transverse holes of the intramedullary rod using a C-arm;
(f) measuring the pose of the tracked adapter with the localizing device;
(g) positioning a drill guide near the bone in the vicinity of the intramedullary rod's transverse holes, said drill guide's pose being read by the localizing device;
(h) projecting a graphic representation of the drill guide on the picture plane defined by coordinate frame G, such that the graphic representation of the drill guide is displayed relative to the graphic representation of the intramedullary rod; and
(i) projecting the graphic representation of the drill guide on one or more x-ray images or similarly oriented picture planes such that the graphic representation of the drill guide is displayed relative to an x-ray image or graphic representation of the intramedullary rod.

9. The method for accurately drilling holes into a long bone of claim 8 further comprising the steps of:
defining a coordinate frame A relative to the tracked adapter;
defining a coordinate frame Z relative to coordinate frame A, the z-axis of the Z coordinate frame being aligned with the long axis of the intramedullary rod, and the origin of coordinate frame Z located at a reference point on the intramedullary rod in the vicinity of the one or more transverse holes;
calculating and recording the pose of coordinate frame A from the measured pose of the tracking adapter; and
adjusting the recorded pose of coordinate frame A such that the origin of coordinate frame Z coincides with the reference point in the x-ray images of the intramedullary rod.

10. The method for accurately drilling holes into a long bone of claim 9 wherein the step of adjusting the recorded pose of coordinate frame A comprises:
selecting an x-ray image of the intramedullary rod containing the reference point;
selecting an axis of the Z coordinate frame that is roughly perpendicular to the long axis of the intramedullary rod and parallel to the plane of the x-ray image;
projecting said axis of the Z coordinate frame onto the image of the rod;
identifying a segment of the image data along the projected line;
applying an image processing algorithm to find the reference point in the segment of image data;
calculating the difference between the reference point and the projected origin of the Z frame; and
calculating an adjustment transformation based on the difference value.

11. The method of claim 10 wherein the reference point is located at the center of the radio-opaque shadow of the intramedullary rod in the segment of image data.

12. The method for accurately drilling holes into a long bone of claim 8 wherein the graphic representation of the drill guide comprises a trajectory line.

13. The method of accurately drilling holes into a long bone of claim 8 wherein the intramedullary rod comprises two or more transverse holes and the step of defining a third coordinate frame G further comprises the steps of positioning the z-axis of the G coordinate frame such that it passes through the centers of the two or more transverse holes to project the holes on the same location on the picture plane.

* * * * *